(12) United States Patent
Garrett

(10) Patent No.: US 9,897,509 B2
(45) Date of Patent: Feb. 20, 2018

(54) FUEL DISPENSING ENVIRONMENT COMPONENT HEALTH MONITORING

(71) Applicant: Gilbarco Inc., Greensboro, NC (US)

(72) Inventor: Ryan Charles Garrett, Randleman, NC (US)

(73) Assignee: Gilbarco Inc., Greensboro, NC (US)

( * ) Notice: Subject to any disclaimer, the term of this patent is extended or adjusted under 35 U.S.C. 154(b) by 132 days.

(21) Appl. No.: 14/729,327

(22) Filed: Jun. 3, 2015

(65) Prior Publication Data

US 2015/0346163 A1 Dec. 3, 2015

Related U.S. Application Data

(60) Provisional application No. 62/007,089, filed on Jun. 3, 2014.

(51) Int. Cl.
*G01N 29/44* (2006.01)
*G01M 3/24* (2006.01)
*G01N 29/14* (2006.01)

(52) U.S. Cl.
CPC .............. *G01M 3/24* (2013.01); *G01N 29/14* (2013.01); *G01N 29/4436* (2013.01); *G01N 29/4454* (2013.01); *G01N 2291/014* (2013.01); *G01N 2291/0258* (2013.01)

(58) Field of Classification Search
CPC .............. G01N 29/14; G01N 29/4436; G01N 29/4454; G01N 29/036; G01M 3/24; G01M 3/38; G01M 3/243
See application file for complete search history.

(56) References Cited

U.S. PATENT DOCUMENTS

| 4,977,528 A | 12/1990 | Norris |
| 5,040,577 A | 8/1991 | Pope |
| 5,319,545 A | 6/1994 | McGarvey et al. |
| 5,361,636 A * | 11/1994 | Farstad ................. G01M 3/243 73/40.5 A |

(Continued)

OTHER PUBLICATIONS

"Augury's Gadget Lets Machines Hear When They're About to Die," Wired, published Nov. 4, 2015, http://www.wired.com/2015/11/augury-lets-machines-hear-when-theyre-about-to-break-down/, accessed Jan. 6, 2016, all enclosed pages cited.

(Continued)

*Primary Examiner* — Helen Kwok
(74) *Attorney, Agent, or Firm* — Nelson Mullins Riley & Scarborough, LLP

(57) ABSTRACT

Methods and systems for monitoring the health and operational status of components in a fuel dispensing environment. In one aspect, a method includes providing a control system having a memory in which is stored information representative of a first vibration characteristic of a component, providing a sensor in electronic communication with the control system, the sensor operative to sense vibration characteristics of the component, and coupling the sensor with the component. The method also includes sensing a second vibration characteristic of the component using the sensor, transmitting information representative of the second vibration characteristic to the control system, and comparing the information representative of the second vibration characteristic to the information representative of the first vibration characteristic.

22 Claims, 6 Drawing Sheets

(56) References Cited

U.S. PATENT DOCUMENTS

| | | | |
|---|---|---|---|
| 5,400,253 A | | 3/1995 | O'Connor |
| 5,423,457 A | | 6/1995 | Nicholas et al. |
| 5,606,130 A | * | 2/1997 | Sinha .................... G01N 29/036 73/599 |
| 5,689,071 A | | 11/1997 | Ruffner et al. |
| 5,734,851 A | | 3/1998 | Leatherman et al. |
| 5,857,500 A | | 1/1999 | Payne et al. |
| 5,883,815 A | * | 3/1999 | Drakulich ............... G01M 3/38 340/501 |
| 5,886,262 A | * | 3/1999 | Sinha .................... G01H 13/00 73/579 |
| 5,939,634 A | * | 8/1999 | Johnson .................. G01F 17/00 73/596 |
| 5,954,080 A | | 9/1999 | Leatherman |
| 5,956,259 A | | 9/1999 | Hartsell, Jr. et al. |
| 6,052,629 A | | 4/2000 | Leatherman et al. |
| 6,067,476 A | | 5/2000 | Siler |
| 6,138,512 A | * | 10/2000 | Roberts .................. G01M 3/243 73/40 |
| 6,435,204 B2 | | 8/2002 | White et al. |
| 6,532,999 B2 | | 3/2003 | Pope et al. |
| 6,712,101 B1 | | 3/2004 | Nanaji |
| 6,935,191 B2 | | 8/2005 | Oliver et al. |
| 6,959,837 B2 | | 11/2005 | Shermer et al. |
| 7,010,961 B2 | | 3/2006 | Hutchinson et al. |
| 7,289,877 B2 | | 10/2007 | Wilson |
| 7,954,386 B2 | | 6/2011 | Nanaji et al. |
| 8,291,928 B2 | | 10/2012 | Reid et al. |
| 8,872,651 B2 | | 10/2014 | Reid et al. |
| 9,302,899 B2 | | 4/2016 | Williams et al. |
| 9,523,597 B2 | | 12/2016 | Williams et al. |
| 2003/0079774 A1 | | 5/2003 | Reyman |
| 2003/0233206 A1 | * | 12/2003 | White .................... F17C 5/007 702/116 |
| 2010/0071469 A1 | | 3/2010 | Luo |
| 2010/0139782 A1 | * | 6/2010 | Deline ................... B67D 7/16 137/87.03 |
| 2011/0040503 A1 | * | 2/2011 | Rogers ................... B67D 7/222 702/55 |
| 2012/0078741 A1 | | 3/2012 | Deline |
| 2013/0126553 A1 | | 5/2013 | Williams |
| 2015/0149284 A1 | | 5/2015 | Williams et al. |
| 2016/0034899 A1 | * | 2/2016 | Myers ................... H04B 5/0081 705/44 |

OTHER PUBLICATIONS

International Search Report dated Sep. 2, 2015 for corresponding PCT Application No. PCT/US2015/34006.

Written Opinion of the International Searching Authority dated Sep. 2, 2015 for corresponding PCT Application No. PCT/US2015/34006.

* cited by examiner

FUEL DISPENSING ENVIRONMENT COMPONENT HEALTH MONITORING

PRIORITY CLAIM

This application claims the benefit of U.S. Provisional Application Ser. No. 62/007,089, titled "Fuel Dispensing Environment Component Health Monitoring," filed Jun. 3, 2014, which is hereby relied upon and incorporated herein by reference for all purposes.

BACKGROUND

The present invention relates generally to equipment used in fuel dispensing environments. More specifically, embodiments of the present invention relate to monitoring the health and/or status of components associated with a fuel dispensing environment using a plurality of sensors, such as acoustic or vibration sensors.

A typical fuel dispensing environment, such as the forecourt of a retail fuel dispensing station, comprises a large number of components both for fuel handling and for conducting fuel dispensing transactions. Examples of such components include fuel dispensers, fuel piping, underground storage tanks, submersible turbine and self-contained pumps, motors, and dispensing nozzles. Further, fuel dispensers themselves typically contain flow meters, pulsers, control electronics, valves, card readers, manifolds, and internal fuel and vapor recovery piping, among many others. Many of these components are subject to regulatory requirements to maintain a high degree of accuracy and safety and to guard against environmental impact.

As is well known, for a variety of reasons, these components require periodic maintenance or replacement. Some of these components tend to wear over time, which can cause a loss of accuracy or efficiency in a fueling transaction or other operational issues. Component wear can be caused by manufacturing defects, poor fuel quality, or excessive use, among other causes. Eventually, the components may fail (e.g., failure of a pump motor or a leak in the fuel piping) leading to downtime while the components are replaced. Further, some of the components may fail to operate properly, leading to customer frustration or the inability to complete a fueling transaction. Moreover, it will be appreciated that there is the potential for fraud with respect to some of these components, such as a fuel flow meter, pulser, and the control electronics.

SUMMARY

The present invention recognizes and addresses various considerations of prior art constructions and methods. According to one embodiment, the present invention provides a method of monitoring at least one component in a fuel dispensing environment. The method comprises providing a control system having a memory, the memory having stored therein information representative of at least one first vibration characteristic of the at least one component. The method also comprises providing at least one sensor in electronic communication with the control system, the at least one sensor operative to sense vibration characteristics of the at least one component. Further, the method comprises coupling the at least one sensor with the at least one component, sensing at least one second vibration characteristic of the at least one component using the at least one sensor, and transmitting information representative of the at least one second vibration characteristic to the control system. Finally, the method comprises comparing the information representative of the at least one second vibration characteristic to the information representative of the at least one first vibration characteristic.

According to another embodiment, the present invention provides a fuel dispenser. The fuel dispenser comprises fuel flow piping for providing fluid communication between a source of fuel and a fueling nozzle. The fuel dispenser also comprises a plurality of fuel handling components disposed along the fuel flow piping and a control system. Further, the fuel dispenser comprises at least one vibration sensor in electronic communication with the control system, the at least one vibration sensor coupled with one of the plurality of fuel handling components. The at least one vibration sensor is operative to sense at least one vibration characteristic of the one of the plurality of fuel handling components. The control system is operative to obtain information representative of the at least one vibration characteristic from the at least one vibration sensor. In addition, the control system is operative to compare the information representative of the at least one vibration characteristic to information about the one of the plurality of fuel handling components stored in memory.

Those skilled in the art will appreciate the scope of the present invention and realize additional aspects thereof after reading the following detailed description of preferred embodiments in association with the accompanying drawing figures.

BRIEF DESCRIPTION OF THE DRAWINGS

A full and enabling disclosure of the present invention, including the best mode thereof directed to one skilled in the art, is set forth in the specification, which makes reference to the appended drawings, in which.

Figure 1:
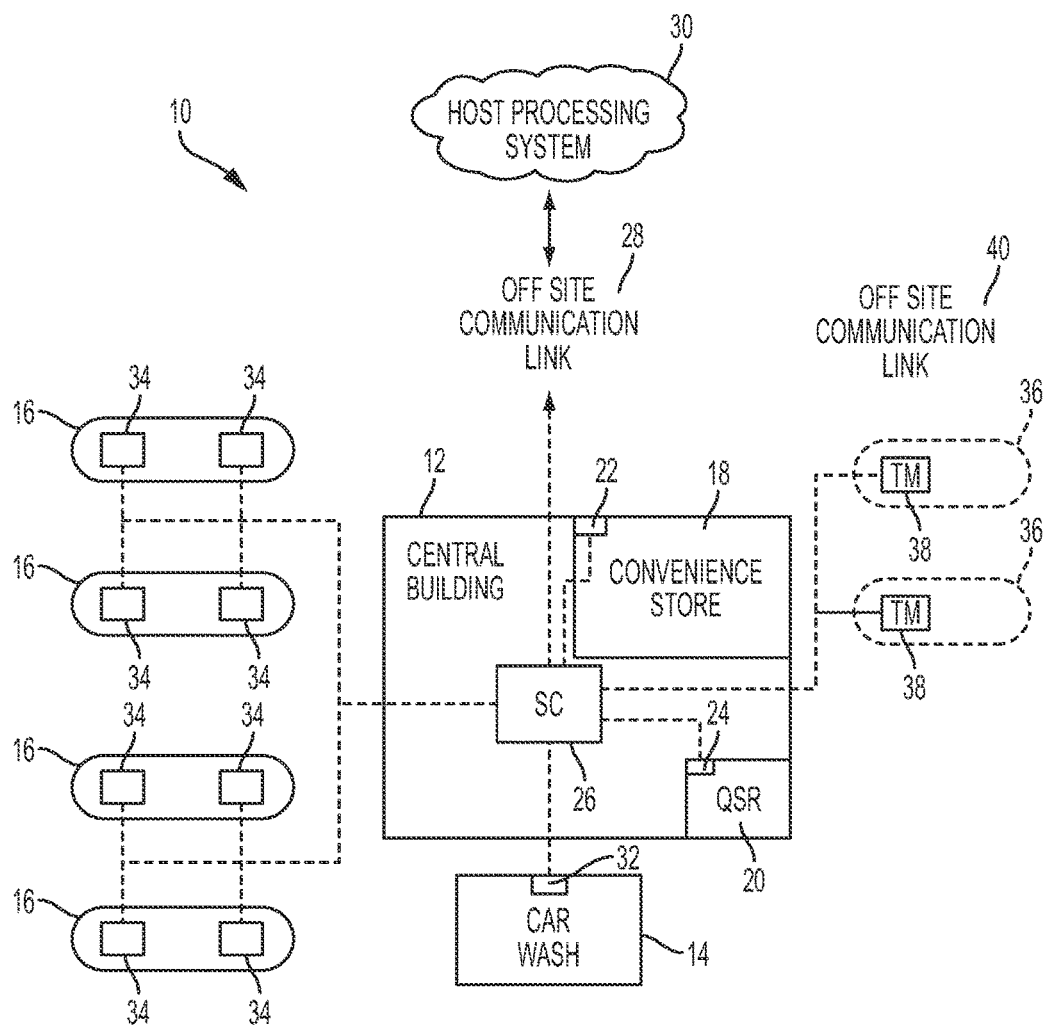
FIG. 1 is a diagrammatic representation of a retail fuel dispensing environment in which an embodiment of the present invention may be utilized.

Repeat use of reference characters in the present specification and drawings is intended to represent same or analogous features or elements of the invention.

DETAILED DESCRIPTION OF PREFERRED EMBODIMENTS

Reference will now be made in detail to presently preferred embodiments of the invention, one or more examples of which are illustrated in the accompanying drawings. Each example is provided by way of explanation of the invention, not limitation of the invention. In fact, it will be apparent to those skilled in the art that modifications and variations can be made in the present invention without departing from the scope or spirit thereof. For instance, features illustrated or described as part of one embodiment may be used on another embodiment to yield a still further embodiment. Thus, it is intended that the present invention covers such modifications and variations as come within the scope of the present disclosure including the appended claims and their equivalents.

Some embodiments of the present invention may be particularly suitable for use with a fuel dispenser in a retail service station environment, and the below discussion will describe some preferred embodiments in that context. However, those of skill in the art will understand that the present invention is not so limited. In fact, it is contemplated that embodiments of the present invention may be used with any fluid dispensing environment and with other fluid dispensers. For example, embodiments of the present invention may also be used with diesel exhaust fluid (DEF) dispensers, compressed natural gas (CNG) dispensers, and liquefied petroleum gas (LPG) and liquid natural gas (LNG) applications, among others.

Referring now to FIG. 1, an exemplary fueling environment 10 may comprise a central building 12, a car wash 14, and a plurality of fueling islands 16. The central building 12 need not be centrally located within the fueling environment 10, but rather is the focus of the fueling environment 10, and may house a convenience store 18 and/or a quick serve restaurant 20 therein. Both the convenience store 18 and the quick serve restaurant 20 may include a point of sale (POS) 22, 24, respectively. POS 22, 24 may comprise a single computer or server operatively connected to an associated card reader and payment terminal. Additionally, POS 22, 24 may include a display, a touch screen, and/or other input devices.

The central building 12 may further house a site controller (SC) 26, which in an exemplary embodiment may be the PASSPORT® POS system, sold by Gilbarco Inc. of Greensboro, N.C., although third party site controllers may be used. Site controller 26 may control the authorization of fueling transactions and other conventional activities as is well understood, and site controller 26 may preferably be in operative communication with each POS. Alternatively, site controller 26 may be incorporated into a POS, such as point of sale 22 if needed or desired.

Further, site controller 26 may have an off-site communication link 28 allowing communication with a remote host processing system 30 for credit/debit card authorization, content provision, reporting purposes or the like, as needed or desired. In one embodiment, communication link 28 may be a stand alone router, switch, or gateway, although it should be appreciated that site controller 26 may additionally perform the functions of, and therefore replace, such a device. The off-site communication link 28 may be routed through the Public Switched Telephone Network (PSTN), the Internet, both, or the like, as needed or desired. Remote host processing system 30 may comprise at least one server maintained by a third party, such as a financial institution. Although only one remote host processing system 30 is illustrated, those of skill in the art will appreciate that in a retail payment system allowing payment via payment devices issued by multiple payment card companies or financial institutions, site controller 26 may be in communication with a plurality of remote host processing systems 30.

Car wash 14 may have a POS 32 associated therewith that communicates with site controller 26 for inventory and/or sales purposes. Car wash 14 alternatively may be a stand alone unit. Note that car wash 14, convenience store 18, and quick serve restaurant 20 are all optional and need not be present in a given fueling environment.

Fueling islands 16 may have one or more fuel dispensers 34 positioned thereon. Fuel dispensers 34 may be similar to, for example, the ENCORE® dispenser sold by Gilbarco Inc. of Greensboro, N.C. but modified for use with the present invention as described herein. Fuel dispensers 34 are in electronic communication with site controller 26 through any suitable link, such as two wire, RS 422, Ethernet, wireless, etc. as needed or desired.

Fueling environment 10 also has one or more underground storage tanks (USTs) 36 adapted to hold fuel therein. As such, USTs 36 may each be a double walled tank. Further, each UST 36 may include a tank monitor (TM) 38 associated therewith. Tank monitors 38 may communicate with fuel dispensers 34 (either through site controller 26 or directly, as needed or desired) to determine amounts of fuel dispensed and compare fuel dispensed to current levels of fuel within USTs 36 to determine if USTs 36 are leaking.

Tank monitor 38 may communicate with site controller 26 and further may have an off-site communication link 40 for leak detection reporting, inventory reporting, or the like. Much like off-site communication link 28, off-site communication link 40 may be through the PSTN, the Internet, both, or the like. If off-site communication link 28 is present, off-site communication link 40 need not be present and vice versa, although both links may be present if needed or desired.

Further information on and examples of fuel dispensers and retail fueling environments are provided in U.S. Pat. Nos. 6,435,204; 5,956,259; 5,734,851; 6,052,629; 5,689,071; 6,935,191; and 7,289,877, all of which are incorporated herein by reference in their entireties for all purposes. An exemplary tank monitor 38 may be the TLS-450 manufactured and sold by the Veeder-Root Company of Simsbury, Conn. For more information about tank monitors and their operation, reference is made to U.S. Pat. Nos. 5,423,457; 5,400,253; 5,319,545; and 4,977,528, all of which are incorporated by reference herein in their entireties for all purposes.

Figure 2:
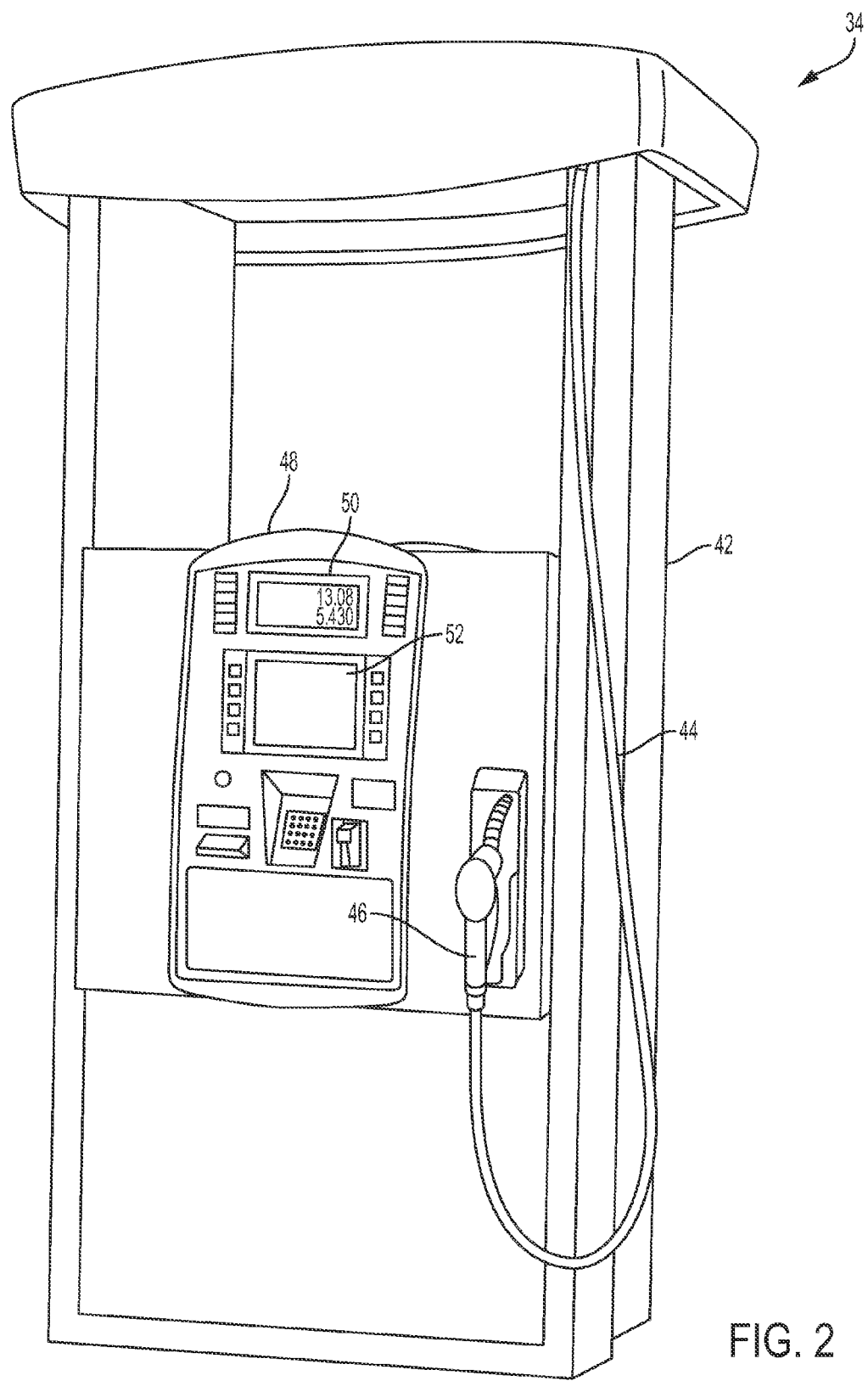
FIG. 2 is a perspective view of an exemplary fuel dispenser that may operate within the retail fueling environment of FIG. 1.

FIG. 2 is a perspective view of an exemplary fuel dispenser 34 that may operate within the fueling environment 10 of FIG. 1. Fuel dispenser 34 includes a housing 42 with a flexible fuel hose 44 extending therefrom. Fuel hose 44 terminates in a manually-operated nozzle 46 adapted to be inserted into a fill neck of a vehicle's fuel tank. Nozzle 46 includes a fuel valve. Various fuel handling components, such as valves and meters, are also located inside of housing 42. These fuel handling components allow fuel to be received from underground piping and delivered through hose 44 and nozzle 46 to a vehicle's tank, as is well understood.

Fuel dispenser 34 has a customer interface 48. Customer interface 48 may include an information display 50 relating to an ongoing fueling transaction that includes the amount of fuel dispensed and the price of the dispensed fuel. Further, customer interface 48 may include a media display 52 to provide advertising, merchandising, and multimedia presentations to a customer in addition to basic transaction functions. The graphical user interface provided by the dispenser allows customers to purchase goods and services other than fuel at the dispenser. Further, display 52 may provide instructions to the customer regarding the fueling transaction.

Figure 3:
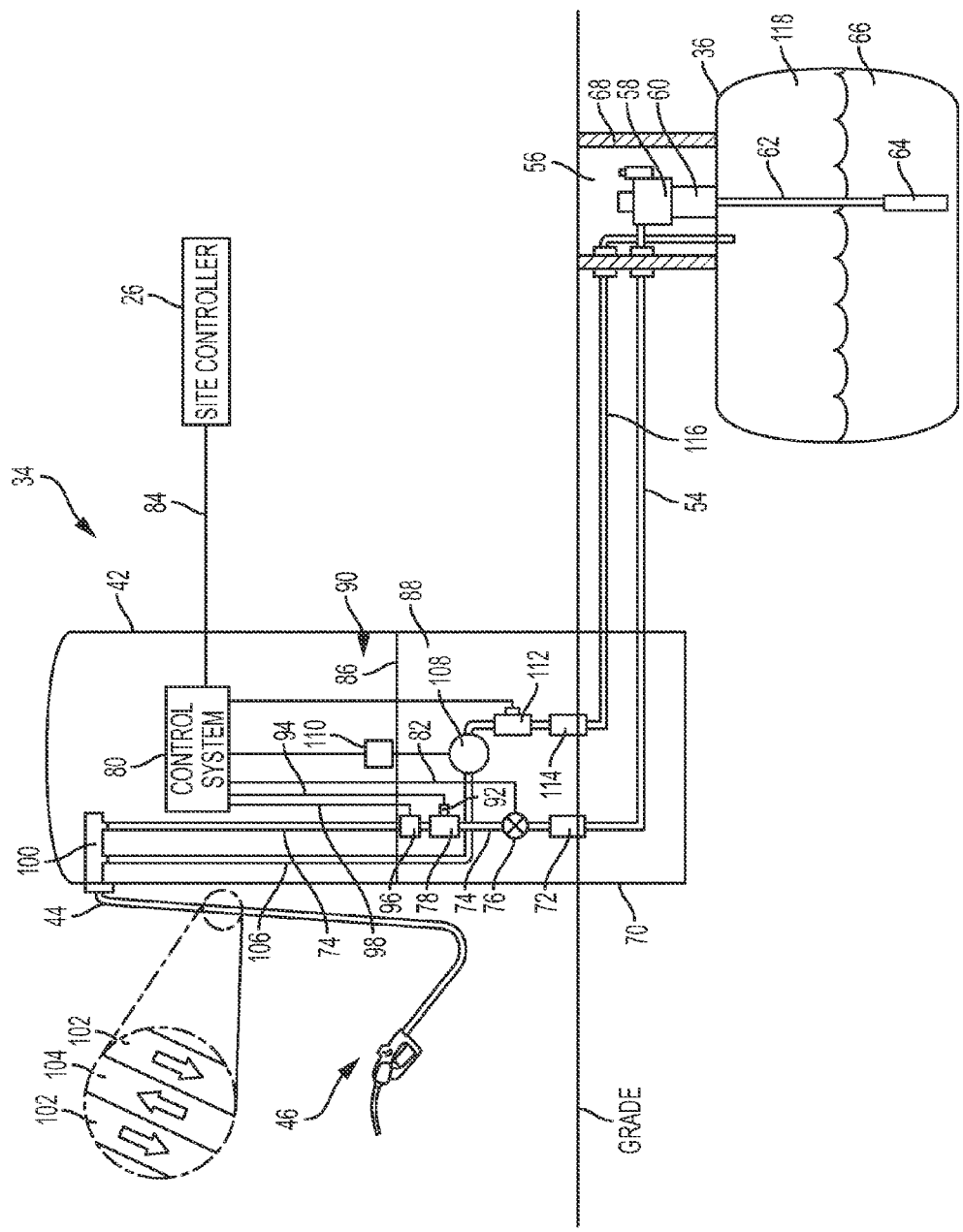
FIG. 3 is a schematic illustration of internal fuel flow components of a fuel dispensing system including the dispenser of FIGS. 1 and 2 and the underground storage tank of FIG. 1 according to an embodiment of the present invention.

FIG. 3 is a schematic illustration of internal fuel flow components of a fuel dispensing system, including a fuel dispenser 34 and a UST 36, according to an embodiment of the present invention. In general, fuel may travel from a UST 36 via main fuel piping 54, which may be a double-walled pipe having secondary containment as is well known, to fuel dispenser 34 and nozzle 46 for delivery. An exemplary underground fuel delivery system is illustrated in U.S. Pat. No. 6,435,204, hereby incorporated by reference in its entirety for all purposes.

More specifically, a submersible turbine pump (STP) 56 associated with the UST 36 is used to pump fuel to the fuel dispenser 34. However, some fuel dispensers may be self-contained, meaning fuel is drawn to the fuel dispenser 34 by a pump controlled by a pump unit positioned within housing 42.

STP 56 is comprised of a distribution head 58 containing power and control electronics that provide power through a riser 60 down to a boom 62 inside the UST 36, eventually reaching a turbine pump contained inside an outer turbine pump housing 64. STP 56 may preferably be the RED JACKET® submersible turbine pump, manufactured by the Veeder-Root Co. of Simsbury, Conn. Also, STP 56 may contain a siphon that allows the STP 56 to generate a vacuum using the force of fuel flow. In addition, riser pipe 60 and distribution head 58 may be secondarily contained to capture and monitor leaks. For example, such a system is disclosed in U.S. Pat. No. 7,010,961, hereby incorporated by reference in its entirety for all purposes. As noted above, there may be a plurality of USTs 36 and STPs 56 in a service station environment if more than one type or grade of fuel 66 is to be delivered by a fuel dispenser 34.

The turbine pump operates to draw fuel 66 upward from the UST 36 into the boom 62 and riser 60 for delivery to the fuel dispenser 34. After STP 56 draws the fuel 66 into the distribution head 58, the fuel 66 is carried through STP sump 68 to main fuel piping 54. Main fuel piping 54 carries fuel 66 through dispenser sump 70 to the fuel dispenser 34 for eventual delivery. Those of skill in the art will appreciate that dispenser sump 70, which may also be double-walled, is adapted to capture any leaked fuel 66 that drains from fuel dispenser 34 and its fuel handling components so that fuel 66 is not leaked into the ground.

Main fuel piping 54 may then pass into housing 42 through a product line shear valve 72. As is well known, product line shear valve 72 is designed to close the fuel flow path in the event of an impact to fuel dispenser 34. U.S. Pat. No. 8,291,928, hereby incorporated by reference in its entirety for all purposes, discloses an exemplary secondarily-contained shear valve adapted for use in service station environments. Product line shear valve 72 contains an internal fuel flow path to carry fuel 66 from main fuel piping 54 to internal fuel piping 74, which may also be double-walled.

After fuel 66 exits the outlet of shear valve 72 and enters into internal fuel piping 74, it may encounter a flow control valve 76 positioned upstream of a flow meter 78. In some prior art fuel dispensers, valve 76 may be positioned downstream of the flow meter 78. In one embodiment, valve 76 may be a proportional solenoid controlled valve, such as described in U.S. Pat. No. 5,954,080, hereby incorporated by reference in its entirety for all purposes.

Flow control valve 76 is under control of a control system 80 via a flow control valve signal line 82. In this manner, control system 80 can control the opening and closing of flow control valve 76 to either allow fuel to flow or not flow through meter 78 and on to the hose 44 and nozzle 46. Control system 80 may be any suitable electronics with associated memory and software programs running thereon whether referred to as a processor, microprocessor, controller, microcontroller, or the like. In a preferred embodiment, control system 80 may be comparable to the microprocessor-based control systems used in CRIND and TRIND type units sold by Gilbarco Inc. Control system 80 typically controls other aspects of fuel dispenser 34, such as valves, displays, and the like as is well understood. For example, control system 80 typically instructs flow control valve 76 to open when a fueling transaction is authorized. In addition, control system 80 may be in electronic communication with site controller 26 via a fuel dispenser communication network 84. Site controller 26 communicates with control system 80 to control authorization of fueling transactions and other conventional activities.

The memory of control system 80 may be any suitable memory or computer-readable medium as long as it is capable of being accessed by the control system, including random access memory (RAM), read-only memory (ROM), erasable programmable ROM (EPROM), or electrically EPROM (EEPROM), CD-ROM, DVD, or other optical disk storage, solid-state drive (SSD), magnetic disc storage, including floppy or hard drives, any type of suitable non-volatile memories, such as secure digital (SD), flash memory, memory stick, or any other medium that may be used to carry or store computer program code in the form of computer-executable programs, instructions, or data. Control system 80 may also include a portion of memory accessible only to control system 80.

Flow control valve 76 is contained below a vapor barrier 86 in a hydraulics compartment 88 of fuel dispenser 34. Control system 80 is typically located in an electronics compartment 90 of fuel dispenser 34 above vapor barrier 86. After fuel 66 exits flow control valve 76, it typically flows through meter 78, which preferably measures the flow rate of fuel 66. In some embodiments, meter 78 may be capable of measuring the density and/or temperature of the flowing fuel.

Flow meter 78 may be any suitable flow meter known to those of skill in the art, including positive displacement, inferential, and Coriolis mass flow meters, among others. Meter 78 typically comprises electronics 92 that communicates information representative of the flow rate, density, and/or temperature of fuel to control system 80 via a signal line 94. For example, electronics 92 may typically include a pulser as known to those skilled in the art. In this manner, control system 80 can update the total gallons (or liters) dispensed and the price of the fuel dispensed on information display 50.

As fuel leaves flow meter 78 it enters a flow switch 96. Flow switch 96, which preferably comprises a one-way check valve that prevents rearward flow through fuel dispenser 34, generates a flow switch communication signal via flow switch signal line 98 to control system 80 to communicate when fuel 66 is flowing through flow meter 78. The flow switch communication signal indicates to control system 80 that fuel is actually flowing in the fuel delivery path and that subsequent signals from flow meter 78 are due to actual fuel flow.

After fuel 66 enters flow switch 96, it exits through internal fuel piping 74 to be delivered to a blend manifold 100. Blend manifold 100 receives fuels of varying octane levels from the various USTs and ensures that fuel of the octane level selected by the customer is delivered. After flowing through blend manifold 100, fuel 66 passes through fuel hose 44 and nozzle 46 for delivery to the customer's vehicle.

In this case, fuel dispenser 34 comprises a vapor recovery system to recover fuel vapors through nozzle 46 and hose 44 to return to UST 36. An example of a vapor recovery assist equipped fuel dispenser is disclosed in U.S. Pat. No. 5,040, 577, incorporated by reference herein in its entirety for all purposes. More particularly, flexible fuel hose 44 is coaxial and includes a product delivery line 102 and a vapor return line 104. Both lines 102 and 104 are fluidly connected to UST 36 through fuel dispenser 34. Lines 102 and 104 diverge internal to dispenser 34 at manifold 100, such that product delivery line 102 is fluidly coupled to internal fuel piping 74 and vapor return line 104 is fluidly coupled to internal vapor return piping 106. During delivery of fuel into a vehicle's fuel tank, the incoming fuel displaces air in the fuel tank containing fuel vapors. Vapor may be recovered from the vehicle's fuel tank through vapor return line 104 and returned to UST 36 with the assistance of a vapor pump 108. A motor 110 may operate vapor pump 108. Internal vapor return piping 106 is coupled to a vapor flow meter 112. Vapor flow meter 112, which measures vapor collected by the nozzle 46 when fuel 66 is dispensed, may be used for in-station diagnostics and monitoring or control of vapor recovery. In some embodiments, vapor flow meter 112 may also be a Coriolis mass flow meter.

After the recovered vapor passes through vapor flow meter 112, the recovered vapor passes to vapor line shear valve 114 (which may be analogous to product line shear valve 72). Finally, the recovered vapor returns to UST 36 via vapor return piping 116. Vapor return piping 116 is fluidly coupled to the ullage 118 of UST 36. Thus, the recovered vapor is recombined with the vapor in ullage 118 to prevent vapor emissions from escaping to the atmosphere. The vapors recombine and liquefy into fuel 66.

In accordance with embodiments of the present invention, a fueling environment such as fueling environment 10 may comprise a plurality of sensors which monitor the health and/or status of various components in the fueling environment. Specific exemplary embodiments are described in more detail below with reference to FIGS. 4-5. In general, however, the sensors may be associated with any of the components described above with reference to FIGS. 1-3, among others. For example, fuel dispensers 34, main fuel piping 54, and UST 36 may each have one or more sensors associated therewith (or with individual components therein) for health and usage monitoring, predictive maintenance, and/or condition monitoring.

In some embodiments, the sensors used for monitoring the health and/or status of various components may be acoustic sensors. As used herein, an acoustic sensor may be any transducer suitable for sensing, measuring, monitoring, and/or capturing the characteristics of acoustic signals or waves (including sound waves and vibrations) emitted by components in a fuel dispensing environment. Likewise, the term "acoustic" is used herein to refer to mechanical waves propagating through a variety of media, including within the components themselves, within a liquid, such as fuel, and propagating through the air. Further, the acoustic sensors may comprise or be in electrical communication with one or more amplifiers and/or filters. For example, filters may be used to filter out background noise or frequencies not at interest for a particular component.

In one example, the acoustic sensors may be measurement microphones, hydrophones, or sound level meters capable of converting acoustic signals to electrical signals. Condenser, piezoelectric, fiber optic, and laser microphones, among others, may be used for this purpose. Preferably, the acoustic sensors may be disposed or positioned with respect to each component such that the sensors can monitor and record (and/or transmit to a control system) one or more of the following characteristics of acoustic emissions from each component: frequency, wavelength, amplitude, pressure, intensity, speed, and direction.

In one preferred embodiment, the acoustic sensors may be able to monitor and capture the characteristics of acoustic waves with frequencies between 20 Hz and 20 kHz, but the invention is not so limited. In other words, those of skill in the art will appreciate that the use of the term "acoustic sensors" is not limited to sensors able to monitor and/or capture characteristics of acoustic waves at a particular frequency or range of frequencies. Rather, this term is used broadly herein to refer to sensors capable of monitoring and/or capturing acoustic wave characteristics at any frequency, including but not limited to infrasound, sound, and ultrasound frequencies.

In other embodiments, the sensors used for monitoring the health and/or status of various components may be vibration sensors. The vibration sensors may be coupled directly with a component of interest for sensing the vibrations of the component. In that regard, the vibration sensors may be any type of accelerometers operative to measure characteristics of the component's vibrations, such as displacement, frequency, amplitude, damping, and/or direction of movement, among others, and to convey information representative of these characteristics to a control system for analysis. The accelerometers may be 3-axis accelerometers, though this is not required. In other embodiments, the vibration sensors can be piezoelectric devices or sensitive microphones in contact with the component of interest. In some embodiments, the vibration sensor(s) associated with a component may be provided in a cavity in or on the component and surrounded by a potting material that seals the vibration sensor in the cavity. Further, in some embodiments, the vibration sensors may be in electronic communication with amplifiers and/or filters.

Those of skill in the art are capable of selecting suitable vibration sensors for use in embodiments of the present invention. In one embodiment, however, the vibration sensors may be analogous to the sensors used with the Fluke 810 Vibration Tester offered by Fluke Inc. of Everett, Wash. In another embodiment, the vibration sensors may be analogous to the vibration meters offered by Extech Instruments of Waltham, Mass.

The measurement sensors used may preferably be located in sufficient proximity or otherwise positioned in relation to the components of interest in order to capture the desired acoustic or vibratory characteristics emitted therefrom. Those of skill in the art will appreciate that, depending on the type of sensor used, a given sensor may be located directly on a component, located within a component, mounted on a structure connected to the component, or mounted on a structure not connected to the component. Thus, for example, a given acoustic sensor may be directly coupled to the surface of a component, may be mounted a few inches above the component, or may be mounted one to several feet from the component. It will also be appreciated that, where it is desirable to collect data indicative of the directionality of the sound emitted by a component, this may affect the positioning of the acoustic sensor.

Notably, each component of interest in a fueling environment, when operating properly, may emit a "signature" acoustic or vibratory response that comprises one or more of the above-mentioned characteristics. Prior to operation of the system, this signature may be measured during operation of each component of interest (either as-manufactured or as-installed, or both). In this regard, where a component variably operates at different capacities, it may be necessary to measure the signature over the range of capacities seen in operation. For example, it may be necessary to measure the signature of a flow meter or fuel piping over a range of flow rates, or the signature of a motor running at various speeds. The signature may be stored in a memory of the control system or suitable memory in communication therewith.

Further, certain actions taken with respect to certain components may likewise have a specific or signature acoustic or vibratory response. These actions may include, for example, dropping or slamming a nozzle onto the ground, repetitive user actions (such as multiple card swipes or repeated lifting of the nozzle boot) indicating problematic equipment, attacking a pulser with tools to break a secure linkage, vehicle impacts with a fuel dispenser, and tampering with a card reader. Other actions indicative of customer frustration, such as repeated attempts to select a grade of fuel using a "grade select" button or overly forceful return of a nozzle to a nozzle boot, may similarly have a characteristic acoustic or vibratory response. Further, sounds characteristic to cracking plastic could indicate lens or door damage. Any such signatures may likewise be stored at the control system or a suitable memory prior to operation.

The sensors may be in wired or wireless electronic communication with each other and/or with a suitable control system, such as site controller 26 or tank monitor 38, described above, which may receive data transmitted by the sensors and analyze data captured by the sensors. In particular, the control system may compare the captured data with the predetermined signature for the component(s) of interest to determine the health and/or status of a given component. The control system's analysis may indicate that the signature has changed, which may in turn indicate current or upcoming maintenance needs. Data which indicates a change in health or operational status may have value(s) of an expected acoustic or vibratory characteristic (such as frequency or wavelength) which exceed or fall below a predetermined threshold (with or without a margin of error) once or multiple times over a predetermined period of time. In one embodiment, the control system may be operative to perform analysis in a manner similar to the Fluke 810 Vibration Tester, mentioned above, or to other commercially available analysis software.

For example, dirty fuel or an out-of-spec part may cause a fuel flow meter to wear over time, which may change the meter's signature response in a measurable way. Likewise, excessive vibration of a hydraulic component may cause that component's (or another component's) signature to change. Further, a lack of any acoustic or vibratory response may indicate that a component has failed altogether.

In alternative embodiments, one or more of the sensors may themselves comprise a suitable control system, to which other acoustic or vibration sensors are connected. Further, the control system may be in communication with the plurality of sensors via the Internet (e.g., via off-site communication link 28) in one embodiment. Thus, the control system may be located on a "cloud" server or the like.

In any event, after it has analyzed data from one or more sensors associated with a given component, the control system may take appropriate action based on its analysis with respect to the component. For example, the control system may alert the appropriate personnel at the fuel dispensing environment of a need for maintenance at the particular component. Alternatively, the control system may sound an alarm, flag a dispenser for evaluation, stop operation of the component (or fuel dispenser housing the component), or take another appropriate action.

Figure 4:
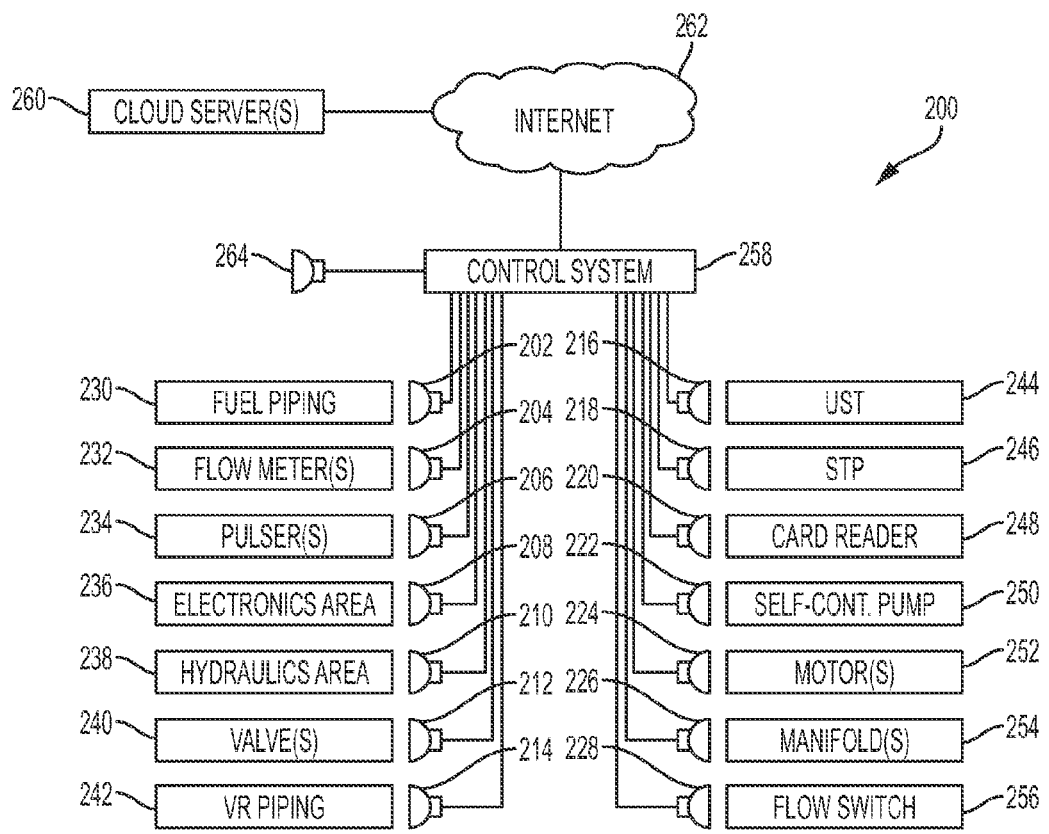
FIG. 4 is a schematic representation of a plurality of networked acoustic sensors associated with components in a fuel dispensing environment in accordance with an embodiment of the present invention.

Based on the foregoing, exemplary embodiments are discussed in detail with reference to FIGS. 4-5. FIG. 4 is a schematic representation of a plurality of networked acoustic sensors associated with components in a fuel dispensing environment 200. As shown, acoustic sensors may be associated with any component in fueling environment 200 for which it is necessary or desirable to obtain health and/or status information. In the illustrated embodiment, acoustic sensors 202-28 may be associated with components 230-56, respectively. These components may be fuel piping 230 internal to a fuel dispenser; one or more flow meter(s) 232 located within a fuel dispenser hydraulics compartment; one or more pulser(s) 234 coupled with flow meters 232; the electronics compartment 236 of a fuel dispenser; the hydraulics compartment 238 of a fuel dispenser; valve(s) 240, such as shear valves 240a or flow control valves 240b, either within or external to a fuel dispenser; vapor recovery piping 242 within a fuel dispenser; an underground storage tank 244 located within fuel dispensing environment 200; a submersible turbine pump 246 associated with UST 244; a card reader 248 associated with a fuel dispenser; a self-contained pump 250 located within the hydraulics compartment of a fuel dispenser; motor(s) 252 operative to drive self-contained pump 250 or other motor(s); manifold(s) 254 within a fuel dispenser, for example at which fuel and/or vapor recovery piping meet; and a flow switch 256 within a fuel dispenser. As noted above, however, in other embodiments other components may be associated with and monitored by an acoustic sensor, and not all of the components in FIG. 4 may be monitored simultaneously or at all. Moreover, in other embodiments, some or all of the components in FIG. 4 may be monitored by vibration sensors.

As shown, acoustic sensors 202-28 are in electronic communication with a control system 258. Control system 258 may preferably be analogous to site controller 26 or fuel dispenser control system 80, described above, or another suitable control system. Further, control system 258 may be wired or wirelessly connected with one or more cloud servers 260 via the internet 262.

Finally, an acoustic sensor 264 may be in electronic communication with control system 258. Acoustic sensor 264 may not be associated with a particular component and may instead measure and/or capture background or baseline acoustic levels which control system 258 (or another control system) may use in analyzing the health and/or status of one of components 230-56. For example, acoustic sensor 264 may be disposed in the hydraulics compartment of a fuel dispenser or coupled with the exterior of a fuel dispenser in order to measure and/or capture background or baseline acoustic levels at these locations. Control system 258 may then filter background levels from acoustic sensor 264 from the data captured for a particular component (e.g., a meter in the hydraulics compartment) to isolate the acoustic waves emitted by the particular component.

Figure 5:
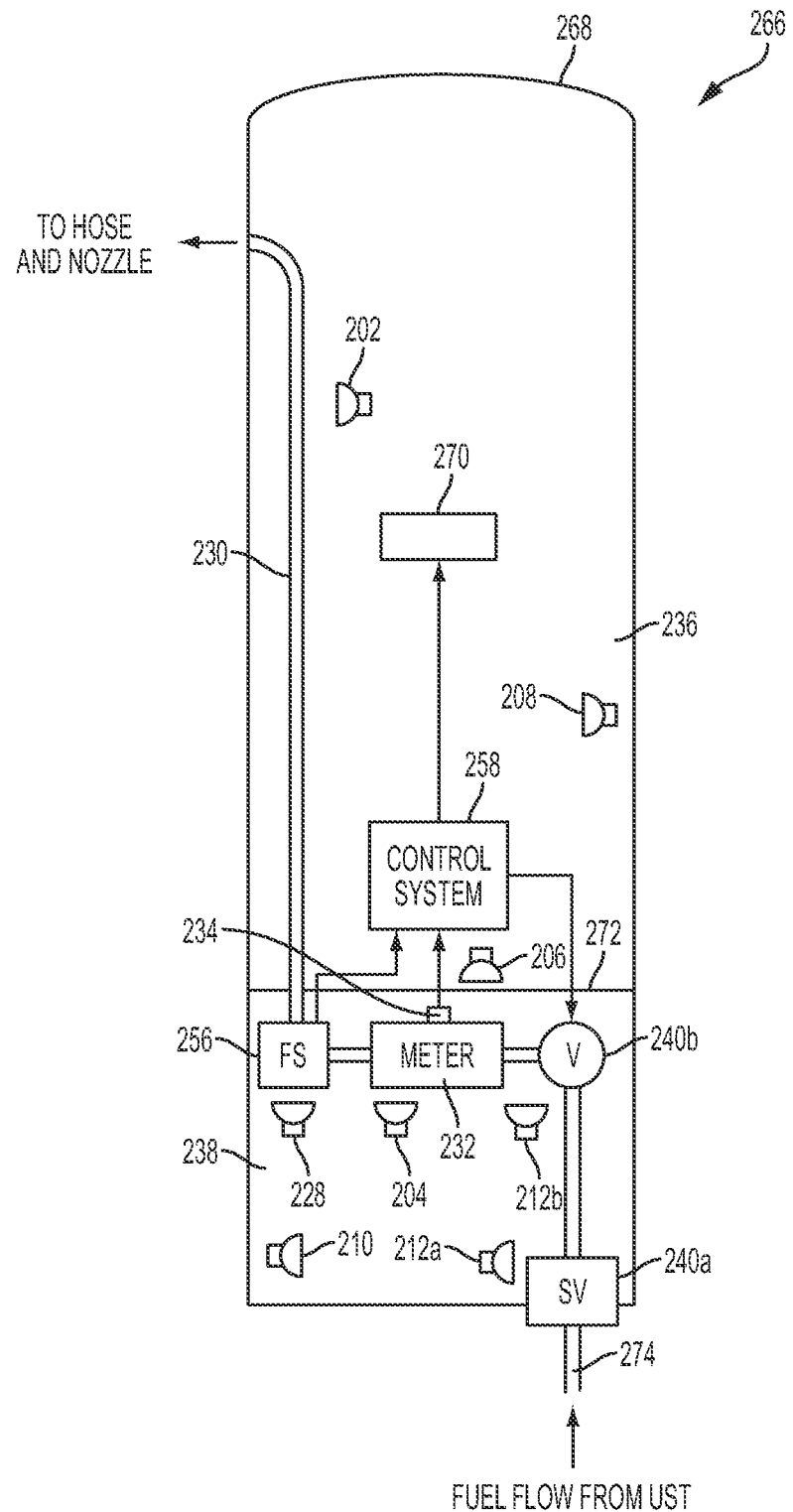
FIG. 5 is a schematic diagram of a fuel dispenser comprising a plurality of acoustic sensors associated with certain of the components of the fuel dispensing environment of FIG. 4 in accordance with an embodiment of the present invention.

FIG. 5 is a schematic representation of a fuel dispenser 266 which may operate in fueling environment 200 and which incorporates some of the components illustrated in FIG. 4. Fuel dispenser 266 includes a housing 268 comprising control system 258, described above. Control system 258 is in electronic communication with an information display 270. A vapor barrier 272 delimits hydraulics compartment 238 of fuel dispenser 266, and control system 258 is located in electronics compartment 236 above vapor barrier 272. As noted above with respect to FIG. 4, in this embodiment acoustic sensors 208 and 210 may be located in electronics compartment 236 and hydraulics compartment 238, respectively. Further, both acoustic sensors 208, 210 are in electronic communication with control system 258.

As explained above, fuel may travel from an underground storage tank via main fuel piping 274 to fuel dispenser 266 for delivery. Main fuel piping 274 may pass into housing 266 first through shear valve 240a. Shear valve 240a contains an internal fuel flow path to carry fuel from main fuel piping 274 to internal fuel piping 230. Again, in this embodiment acoustic sensor 212a is preferably associated with shear valve 240a and is in electronic communication with control system 258.

After fuel exits the outlet of shear valve 240a and enters into internal fuel piping 230, it may encounter flow control valve 240b positioned upstream of flow meter 232. After fuel exits flow control valve 240b, it flows through meter 232, which measures the volume and/or flow rate of the fuel. Meter 232 is operatively connected to pulser 234, which generates a signal indicative of the volumetric flow rate of fuel and periodically transmits the signal to control system 258. Thus, control system 258 may update the total gallons dispensed and the total price of the fuel dispensed on information display 20. In this embodiment, acoustic sensors 212b, 204, and 206 are associated with flow control valve 240b, flow meter 232, and pulser 234, respectively. Each is preferably in electronic communication with control system 258.

As fuel leaves flow meter 232 it enters flow switch 256, which as explained above preferably includes a one-way check valve that prevents rearward flow through fuel dispenser 266. After the fuel leaves flow switch 256, it exits through internal fuel piping 230 to be delivered through the fuel hose and nozzle for delivery to a customer's vehicle. Also as explained with respect to FIG. 4, in this embodiment acoustic sensors 228 and 202 may be respectively associated with flow switch 256 and internal fuel piping 230 and in electronic communication with control system 258.

In operation, depending on the number of acoustic sensors 202-28, 264 in use at a given time, acoustic sensors 202-28, 264 may monitor the acoustic waves emitted from their associated components 230-56 and convert these acoustic waves into electrical signals. Further, acoustic sensors 202-28, 264 may transmit this information to control system 258, which may convert the electrical signals to information representative of one or more of the characteristics noted above (to the extent this step has not already been performed at acoustic sensors 202-28, 264) and analyze this information to determine the health and/or operational status of each component. Where the analysis indicates no change from predetermined threshold or signature acoustic responses for each component, control system 258 may do nothing (i.e., the component is "healthy"). Where the analysis indicates that acoustic characteristics have risen above or fallen below predetermined threshold levels or otherwise do not correspond to predetermined signature acoustic responses for any component, control system 258 may take appropriate action to alert personnel to the need for maintenance, prevent fraud, prevent leakage, halt a fueling transaction, or another appropriate action.

Figure 6:
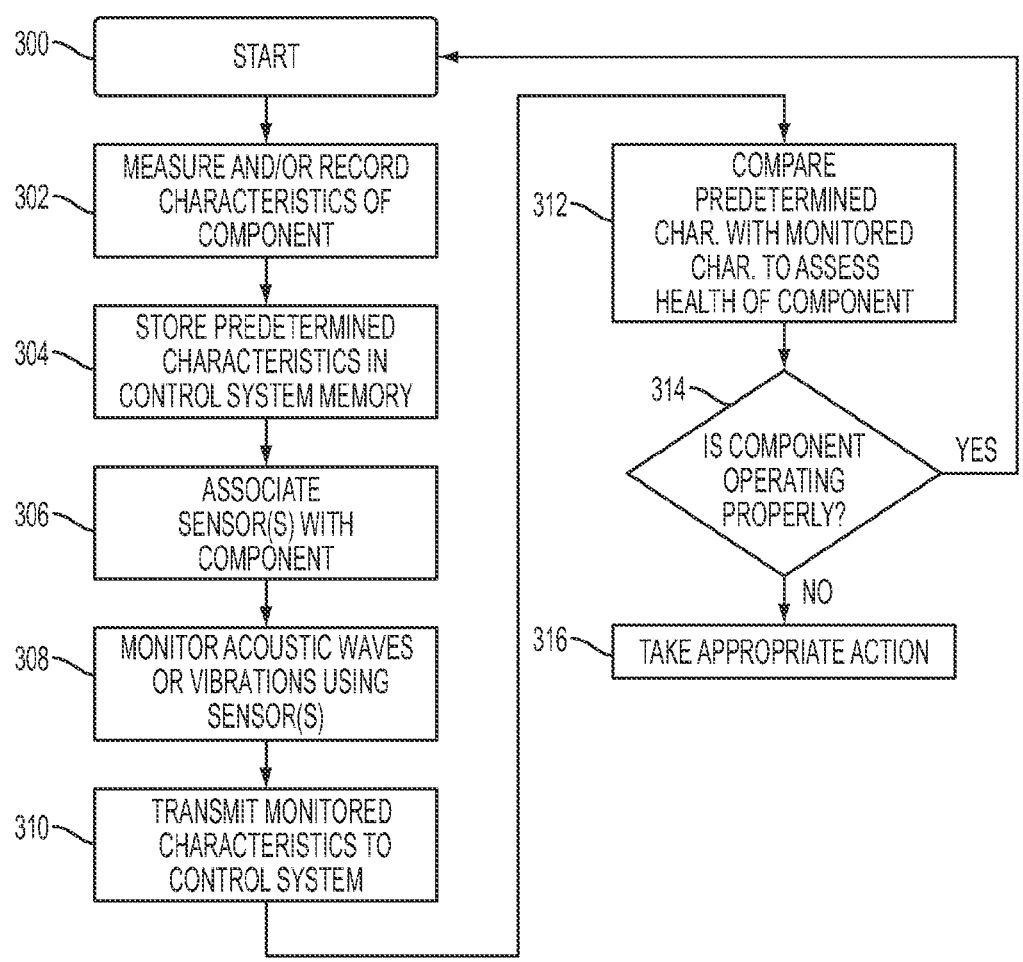
FIG. 6 is a flow chart illustrating steps of a method of monitoring a component associated with a fuel dispensing environment using one or more sensors according to an embodiment of the present invention.

FIG. 6 is a flow chart illustrating steps of a method of monitoring a component associated with a fuel dispensing environment using one or more sensors according to an embodiment of the present invention. The method starts (step 300) and various characteristics associated with acoustic signals and/or vibrations of the component, such as those mentioned above, are measured and recorded (step 302). Preferably, these measurements may be taken for the component as it is installed in the fuel dispensing environment and during steady-state operation. These predetermined characteristics, which may represent a "signature" response of the component, may then be stored in the memory of a control system, such as site controller 26 or tank monitor 38 (step 304). In addition, one or more sensors, which are preferably in electronic communication with the control system, may be associated with the component (step 306). As noted above, the sensors are preferably located in sufficient proximity to the component to capture the desired characteristics. Next, the sensor(s) may monitor acoustic waves and/or vibrations (as the case may be) emitted by the component (step 308) and transmit monitored characteristics to the control system (step 310). The control system then preferably compares the predetermined characteristics previously stored in memory to the monitored characteristics received from the sensor(s) (step 312).

Based on this comparison, the control system may determine, for example, whether the component is operating properly (step 314). In particular, the control system may determine that one of the monitored characteristics falls outside of a margin of error with respect to the corresponding predetermined characteristic. In other embodiments, as explained above, the control system may instead determine whether the monitored characteristics match a signature response of a particular action, such as tampering with a card reader or pulser or repetitive user actions which may indicate equipment problems. In any event, if the component is operating properly, the method restarts at step 300. If not, however, the control system may take appropriate action, such as notifying maintenance personnel, sounding an alarm, or stopping a fueling transaction (step 316).

In other embodiments, in addition to providing acoustic sensor(s) to monitor a component in a fuel dispensing environment, one or more actuators may be provided to excite the component in a predetermined fashion to induce acoustic waves in the component. The acoustic sensor(s) may sense the mechanical vibrations induced in the component and output electrical signals representative of their acoustic characteristics. Characteristics of the acoustic signals monitored and/or recorded by the acoustic sensors(s) may be analyzed to determine the health of a component. For example, acoustic waves may be induced in a UST, and the acoustic response may differ depending on the liquid level in the tank. If the acoustic response is indicative of a liquid level that is less than the liquid level measured by an automated tank gauge or tank monitor, this may indicate that the automated tank gauge or tank monitor is not working properly or that a leak is occurring. Similarly, acoustic waves may be induced in fuel flow piping that is expected to be filled with fuel during normal operation. If the pipe is not filled, e.g., because a leak is occurring, the acoustic response will differ measurably from a predetermined acoustic response based on "healthy" fuel flow piping. Accordingly, the control system may take appropriate action in response to the potential leak.

Those of skill in the art are familiar with suitable actuators for this purpose. In one embodiment, however, the actuators may be analogous to actuators used to vibrate Coriolis flow meters in a prescribed oscillatory bending-mode of vibration.

Notably, the method described above with reference to FIG. 6 may be modified in accordance with this embodiment. In this regard, step 302 described above may also comprise measuring and recording the acoustic response detected at the acoustic sensor(s) when the actuator is used to induce acoustic waves in a healthy component. At step 304, this acoustic response may be stored in memory. After the acoustic sensor(s) are associated with the component of interest at step 306, the method may include the additional steps (not shown in FIG. 6) of associating an actuator or actuators with the component and inducing acoustic waves in the component. Characteristics of the induced acoustic waves may be monitored as described above at step 308, and these characteristics may be transmitted to the control system at step 310. At step 312, the control system may compare the acoustic characteristics previously stored in memory to the monitored acoustic characteristics received from the acoustic sensor(s). And finally, at step 314, based on this comparison, the control system may determine whether the component is operating properly, as described above. At step 316, the process again ends.

In addition to monitoring the health of components in a fuel dispensing environment, this embodiment may also be used to confirm proper operation and/or sensitivity of the acoustic sensor(s). For example, an acoustic wave with predetermined sound characteristics may be induced in a component that is monitored by an acoustic sensor. If the acoustic sensor detects the predetermined characteristics of the induced acoustic wave with appropriate precision, the control system may verify that the acoustic sensor is operating properly.

According to a further embodiment, a single acoustic sensor may be used to monitor more than one component in a fuel dispensing environment. In this regard, because acoustic waves travel through fuel itself and through and along solid components, one acoustic sensor could be used to monitor acoustic waves emitted by all or some of the components along a single fuel product's dispensing path (e.g., all meters in a dispenser associated with a particular fuel product). Further, the acoustic sensor need not be located proximate the components of interest, and it could instead be located upstream of the components, for example along a single section of piping. The acoustic waves would propagate from the components of interest along the piping and/or through the air to the acoustic sensor. Moreover, the control system may use algorithms which analyze the information received from the acoustic sensor and, using predetermined acoustic characteristics known to be associated with given components, filter the information into acoustic characteristics emitted by each component of interest. Thereby, even where a single acoustic sensor is used to monitor multiple components, the control system may identify the health and/or operational status of each component monitored and take appropriate actions with respect to each. Alternatively, the control system may monitor the health and/or operational status of an entire product flow path or a section thereof based on predetermined acoustic characteristics or an acoustic signature associated with the product flow path or section.

According to yet another embodiment, the control system may preferably be operative to treat any abnormal acoustic or vibratory characteristics (e.g., excessive or repetitive abnormal frequencies) as indicative of a maintenance or inspection need, even if the abnormal characteristics are not similar to or associated with a known or predetermined signature of a monitored component.

In a further embodiment, the control system may use information other than acoustic or vibration sensor information to enhance its analysis of the information from the sensor(s). Such other information may include data from a pulser indicative of the flow rate of fuel through a flow meter, data regarding whether a transaction is ongoing, data regarding whether a valve is open or closed, information regarding fuel or component temperature, or data regarding the rate of vapor recovery, among many other types of information. Thus, in one example, if data from the pulser indicates that fuel is not flowing, but the control system receives sensed information from a flow meter indicating that fuel is flowing through the flow meter, the control system may conclude that the pulser is not operating properly or that fraud has occurred.

In other embodiments, one or more sensors may be positioned in a fluid path, such as within internal fuel flow and/or vapor recovery piping. Preferably, such sensors may be configured to detect leakage in the fluid path, such as through small orifices in a flow meter or valve. In this regard, predetermined acoustic or vibration characteristics indicative of normal fluid flow may be stored in the control system, and this information may be compared with acoustic characteristics captured by the sensors during operation to detect deviation beyond a predetermined threshold.

Also, as noted above, acoustic sensors may preferably monitor the direction of acoustic waves emitted by components. In some embodiments, this information may be used to reduce the incidence of "false positive" indications of a maintenance or inspection need. For example, if the control system analyzing data from an acoustic sensor detects acoustic characteristics which appear to indicate an attack on a pulser, but the directional information associated with these characteristics indicates that the acoustic wave came from the upper electronics compartment of a fuel dispenser (where the pulser is not located), the control system may conclude that an attack has not occurred.

It can thus be seen that embodiments of the present invention provide novel systems and methods for monitoring the health and/or status of one or more components in a fuel dispensing environment. Notably, embodiments of the present invention may provide advance notice of potential security breaches, component wear or damage, and other operational issues with components in a fuel dispensing environment. Further, embodiments of the present invention provide acoustic and/or vibration "behavioral" analysis of a fuel dispenser or fuel dispensing environment, including internal events, customer-originated events, and potential fraud attacks.

While one or more preferred embodiments of the invention have been described above, it should be understood that any and all equivalent realizations of the present invention are included within the scope and spirit thereof. The embodiments depicted are presented by way of example only and are not intended as limitations upon the present invention. Thus, it should be understood by those of ordinary skill in this art that the present invention is not limited to these embodiments since modifications can be made. Therefore, it is contemplated that any and all such embodiments are included in the present invention as may fall within the scope and spirit thereof.

What is claimed is:

1. A method of monitoring at least one component in a fuel dispensing environment, said method comprising the steps of:

providing a control system having a memory;

providing at least one sensor in electronic communication with said control system, said at least one sensor operative to sense vibration characteristics of said at least one component;

coupling said at least one sensor with said at least one component;

during operation of said at least one component, sensing at least one first vibration characteristic of said at least one component using said at least one sensor;

storing information representative of said at least one first vibration characteristic of said at least one component in said control system memory;

during operation of said at least one component, sensing at least one second vibration characteristic of said at least one component using said at least one sensor;

transmitting information representative of said at least one second vibration characteristic to said control system; and comparing said information representative of said at least one second vibration characteristic to said information representative of said at least one first vibration characteristic.

2. The method of claim 1, further comprising a plurality of sensors in electronic communication with said control system.

3. The method of claim 1, wherein said at least one component is located within a fuel dispenser.

4. The method of claim 1, wherein said at least one first vibration characteristic and said at least one second vibration characteristic are selected from the group consisting of: displacement, frequency, amplitude, damping, and direction of movement.

5. The method of claim 1, wherein said at least one component is selected from the group consisting of: fuel piping, a flow meter, a pulser, a valve, vapor recovery piping, an underground storage tank, a submersible turbine pump, a self-contained pump, a motor, a manifold, and a flow switch.

6. The method of claim 1, further comprising determining whether said information representative of said at least one second vibration characteristic differs from said information representative of at least one first vibration characteristic by a predetermined threshold.

7. The method of claim 6, further comprising notifying an operator of said fuel dispensing environment of a need for maintenance with respect to said at least one component.

8. The method of claim 1, further comprising receiving at said control system information representative of an amount of fuel flowing through a flow meter from a pulser.

9. A method of monitoring at least one component in a fuel dispensing environment, said method comprising the steps of:

providing a control system having a memory, said memory having stored therein information representative of at least one first vibration characteristic of said at least one component;

providing at least one sensor in electronic communication with said control system, said at least one sensor operative to sense vibration characteristics of said at least one component;

coupling said at least one sensor with said at least one component;

sensing at least one second vibration characteristic of said at least one component using said at least one sensor;

transmitting information representative of said at least one second vibration characteristic to said control system;

comparing said information representative of said at least one second vibration characteristic to said information representative of said at least one first vibration characteristic;

receiving at said control system information representative of an amount of fuel flowing through a flow meter from a pulser; and comparing said information representative of said at least one second vibration characteristic with said information representative of said amount of fuel flowing through said flow meter.

10. The method of claim 1, further comprising filtering said information representative of said at least one second vibration characteristic.

11. The method of claim 1, wherein said control system comprises a server located remotely from said fuel dispensing environment.

12. The method of claim 1, wherein said control system comprises a site controller.

13. The method of claim 1, wherein said at least one sensor comprises an accelerometer.

14. A fuel dispenser, comprising:

fuel flow piping for providing fluid communication between a source of fuel and a fueling nozzle;

a plurality of fuel handling components disposed along said fuel flow piping;

a control system;

at least one vibration sensor in electronic communication with said control system, said at least one vibration sensor coupled with one of said plurality of fuel handling components, wherein said one of said plurality of fuel handling components is disposed within a housing of said fuel dispenser;

said at least one vibration sensor operative to sense at least one vibration characteristic of said one of said plurality of fuel handling components;

said control system operative to obtain information representative of said at least one vibration characteristic from said at least one vibration sensor; and said control system operative to compare said information representative of said at least one vibration characteristic to information about said one of said plurality of fuel handling components stored in memory.

15. The fuel dispenser of claim 14, wherein said one of said plurality of fuel handling components is selected from the group consisting of: a fuel flow meter; a pulser; a valve; a flow switch; a manifold; and a pump.

16. The fuel dispenser of claim 14, further comprising a vibration sensor coupled with said fuel flow piping and in electronic communication with said control system.

17. The fuel dispenser of claim 14, wherein said at least one vibration sensor comprises an accelerometer.

18. The fuel dispenser of claim 14, wherein said at least one vibration sensor comprises a piezoelectric sensor.

19. The fuel dispenser of claim 14, wherein said at least one vibration characteristic is selected from the group consisting of: displacement, frequency, amplitude, damping, and direction of movement.

20. The fuel dispenser of claim 14, wherein said control system is operative to determine whether said information representative of said at least one vibration characteristic differs from said information about said one of said plurality of fuel handling components stored in memory by a predetermined threshold.

21. The fuel dispenser of claim 14, wherein said memory is located remotely from said fuel dispenser.

22. The fuel dispenser of claim 14, wherein said at least one vibration sensor comprises a plurality of vibration sensors and each one of said plurality of vibration sensors is coupled with one of said plurality of fuel handling components.

\* \* \* \* \*